(12) United States Patent  
Cappa et al.

(10) Patent No.: US 7,777,140 B2  
(45) Date of Patent: Aug. 17, 2010

(54) IS-4 LEAD TO PSA INTERFACE CABLE

(75) Inventors: Armando M. Cappa, Granada Hills, CA (US); J. Terry Benson, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 12/613,393

(22) Filed: Nov. 5, 2009

(65) Prior Publication Data

US 2010/0048062 A1   Feb. 25, 2010

Related U.S. Application Data

(62) Division of application No. 11/245,770, filed on Oct. 7, 2005, now Pat. No. 7,633,023.

(51) Int. Cl.
*H01R 24/00* (2006.01)
(52) U.S. Cl. .................... 200/51.06; 439/506
(58) Field of Classification Search .............. 200/51.06, 200/52 R; 324/384, 538, 539; 607/27–29; 439/506, 268, 729, 829, 909
See application file for complete search history.

(56) References Cited

U.S. PATENT DOCUMENTS

| | | | |
|---|---|---|---|
| 3,424,979 A | | 1/1969 | Stocker |
| 4,178,052 A | | 12/1979 | Ekbom et al. |
| 5,234,359 A | * | 8/1993 | Takahashi et al. ........... 439/481 |
| 5,334,045 A | | 8/1994 | Cappa et al. |
| 5,557,210 A | | 9/1996 | Cappa et al. |
| 5,679,022 A | | 10/1997 | Cappa et al. |
| 6,192,278 B1 | | 2/2001 | Werner et al. |
| 6,343,233 B1 | | 1/2002 | Werner et al. |
| 7,150,655 B2 | * | 12/2006 | Mastrototaro et al. ....... 439/638 |

OTHER PUBLICATIONS

NonFinal Office Action, mailed Dec. 23, 2008—U.S. Appl. No. 11/245,770.
NonFinal Office Action, mailed Apr. 8, 2009—U.S. Appl. No. 11/245,770.
Notice of Allowance, mailed Oct. 20, 2009—U.S. Appl. No. 11/245,770.

* cited by examiner

*Primary Examiner*—Edwin A. Leon

(57) ABSTRACT

A universal cable connector for detachably connecting a stimulation lead to a system analyzer includes a nonconductive connector block for releasably receiving and holding fixed a proximate contact electrically in continuity with a distal electrode, a cable for selectively electrically interconnecting the proximate contact and the system analyzer, and a switch mechanism for selectively connecting electrically the system analyzer cable with the proximate contact thereby enabling the system analyzer to determine the efficacy of the chosen body tissue site. The connector block includes a nest region for receiving the proximal end of the lead and the switch mechanism includes a switch contact electrically engaged with the cable and movable between a first position disengaged from an associated and selected exposed proximate contact and a second position engaged with the proximate contact for electrically connecting the distal electrode to the system analyzer.

5 Claims, 19 Drawing Sheets

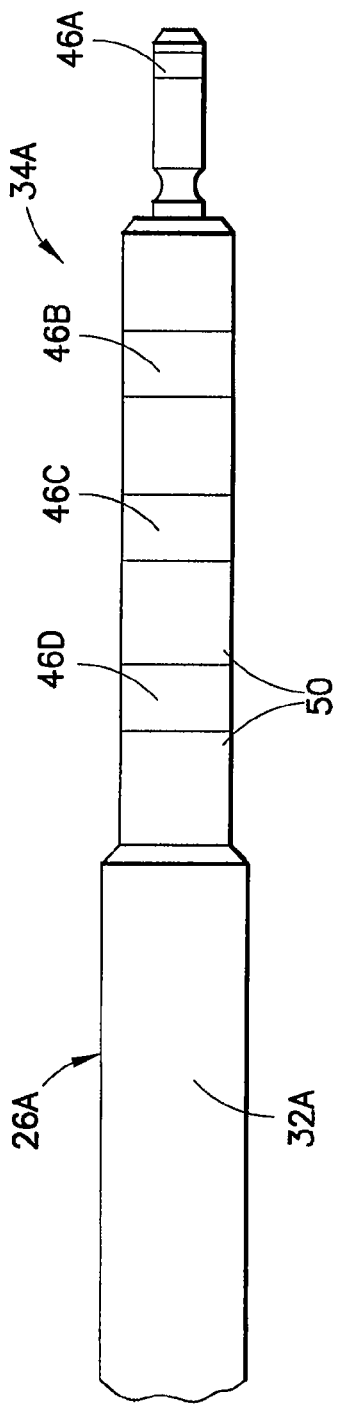
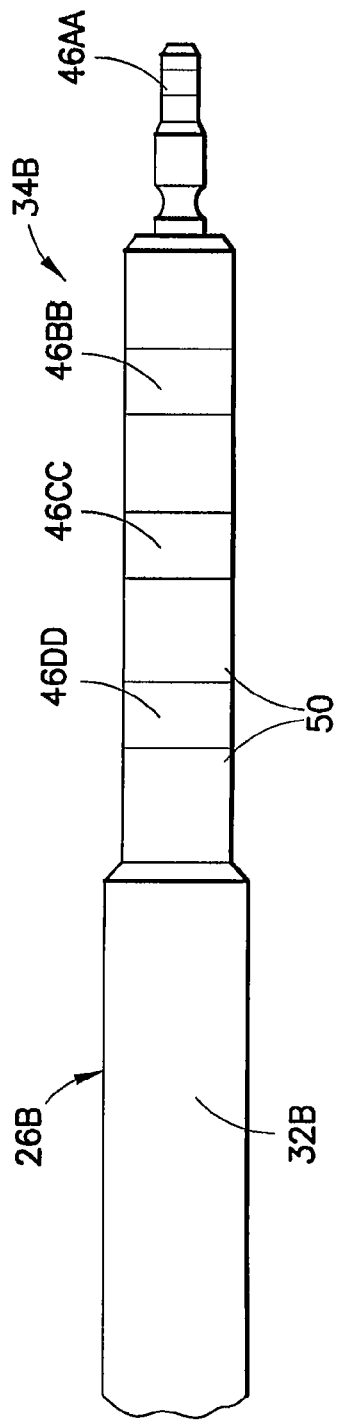
FIG.2A PRIOR ART
FIG.2B PRIOR ART

|  | CONFIGURATION | DESCRIPTION | LEAD MARKING | DEVICE MARKING |
|---|---|---|---|---|
| HIGH VOLTAGE | LLHO | BIPOLAR PACE/SENSE SINGLE SHOCK | DF4-LLHO | DF4-LLHO |
| | LLHH | BIPOLAR PACE/SENSE DUAL SHOCK | DF4-LLHH | DF4-LLHH |
| | LL̲HO̲ | BIPOLAR PACE/SENSE SINGLE SHOCK: INTEGRATED | DF4-LL̲HO̲ | DF4-LLHO |
| | LL̲HH̲ | BIPOLAR PACE/SENSE DUAL SHOCK: INTEGRATED | DF4-LL̲HH̲ | DF4-LLHH |
| | OOHH | DUAL SHOCK | DF4-OOHH | DF4-OOHH |
| LOW VOLTAGE | LLLO | TRIPOLAR PACE/SENSE | IS4-LLLO | IS4-LLLO |
| | LLLL | QUADRIPOLAR PACE/SENSE | IS4-LLLL | IS4-LLLL |

NOMENCLATURE
L=LOW VOLTAGE CONTACT
H=HIGH VOLTAGE CONTACT
O=OPEN (NON-ACTIVE)

FIG. 3
PRIOR ART

IS-4 LEAD TO PSA INTERFACE CABLE

CROSS-REFERENCE TO RELATED APPLICATIONS

This application is a division of U.S. patent application Ser. No. 11/245,770, filed Oct. 7, 2005, titled "IS-4 Lead to PSA Interface Cable".

FIELD OF THE INVENTION

The present invention relates generally to implantable medical devices for providing stimulating pulses to selected body tissue, and more particularly, to a universal cable connector which easily permits a system analyzer used during an implant procedure to be releasably connected to proximate contacts of a stimulation lead enabling the performance of various tests during the procedure.

BACKGROUND OF THE INVENTION

Most implantable stimulation devices, such as pacemakers and ICDs, use one or more implantable stimulation leads that electrically connect the stimulation device to a desired body tissue location. There are numerous types of implantable stimulation leads, just as there are numerous types of implantable stimulation devices. Implantable stimulation leads include sensing/pacing leads, shocking leads, epicardial leads, endocardial leads, atrial leads, ventricular leads, unipolar leads, bipolar leads, and the like.

All implantable stimulation leads include one or more electrodes at a distal end of the lead, and an electrical connector at a proximal end of the lead. The distal electrode is adapted to physically and/or electrically contact body tissue at a desired monitoring and/or stimulating location. Active or passive fixation means may also be included as part of the lead at or near the distal end in order to secure the electrode in its desired tissue-contacting location. The proximal connector is adapted to interface with the implantable stimulation device. Connecting the distal electrode to the proximal connector is the lead body. The lead body comprises one or more flexible electrical conductors, surrounded or otherwise protected by an appropriate insulating sheath, which establishes electrical connection between the distal electrode and the proximal connector. As used herein, and as is conventional when describing implantable stimulation leads, the "distal" end of a lead is the end farthest from the stimulation device, and the "proximal" end is the end closest to, and usually the end connected to, the stimulation device.

When an implantable stimulation lead is first implanted in a patient, there are some preliminary electrical tests that should be performed before the lead is finally attached to its corresponding stimulation device. For example, if the lead is a pacing lead that is to be connected to an implantable pacemaker, then the lead is first implanted (e.g., transvenously) so that the distal electrode is in electrical contact with cardiac muscle tissue. Then, before the proximal connector of the lead is secured to the pacemaker, the proximal connector is temporarily connected to an appropriate testing device (e.g., a patient system analyzer) so that a series of stimulation pulses of varying energies, or other test signals (such as signals to measure the lead impedance), can be applied to the cardiac tissue through the lead in order to ascertain the capture threshold at which the cardiac muscle tissue contracts, or in order to determine other parameters associated with the lead. The results of such capture threshold testing, or other testing, advantageously provide an indication as to whether the distal electrode is making good contact with the body tissue, as well as what the initial setting of the stimulation energy of the pacemaker should be.

If the lead is a shocking lead, also referred to as a defibrillation lead, then typically at least two shocking leads are implanted so that the distal electrodes contact the appropriate cardiac tissue. The distal electrodes may comprise patch electrodes or any other appropriate shocking electrodes. The proximal connectors of such leads are then temporarily connected to an appropriate testing device, typically referred to as a "defibrillation system analyzer (DSA)".

The defibrillation system analyzer applies an appropriate signal (usually a low amplitude AC signal) to the shocking electrodes in order to induce fibrillation. Shocking pulses of varying energies are then applied to the cardiac tissue across the shocking electrodes in order to ascertain the defibrillation threshold, i.e., the amount of energy required in a defibrillation shock pulse in order to defibrillate the heart. Such defibrillation threshold is then used to guide the initial setting of the defibrillation energy generated by the ICD.

Although the present invention is directed primarily towards a universal cable connector for temporarily connecting implantable shocking leads and implantable shocking devices with a defibrillation system analyzer, it may be appreciated that the present invention may also be used with implantable pacing leads, an implantable pacemaker and a patient system analyzer (i.e., a system analyzer which is used to test an implantable pacemaker or ICD). Thus, it shall be understood that "implantable stimulation leads" shall include both pacing and shocking leads, "implantable stimulation device" shall include both pacing and shocking devices, and "system analyzers" shall include both pacing and defibrillation system analyzers.

Proximal connectors used with most implantable stimulation leads are typically one of two types: unipolar or bipolar. Unipolar proximal connectors include a single proximal tip electrode (male connector) adapted to be inserted into an appropriate conductive annular ring or other receiving receptacle (female connector) located on or in the implantable stimulation device. Secure physical and electrical contact between the male and female connectors is typically obtained using a setscrew. That is, the setscrew is threadedly mounted in the female connector and is tightened against the male connector so as to firmly hold it in physical and electrical contact with the female connector. In order for a proper connection to be made, it is necessary that the male connector and female connectors be of the same size.

Bipolar proximal connectors typically include a proximal tip electrode the same as is used in proximal unipolar connectors, and also include a proximal ring electrode, that is an annular conductive ring that is spaced-apart from the tip electrode. The receiving, or female bipolar, connector thus comprises an appropriate receiving channel having separate conductive elements therein that establish a secure physical and electrical connection with the proximal tip and ring electrodes of the lead. A setscrew, or equivalent, may also be used to secure one or both of the tip and ring electrodes within the female connector.

Some effort has been made in recent years to standardize the size of proximal connectors used with pacing leads. However, there still exists a wide variety of different sizes and types of proximal connectors that are used with implantable stimulation devices. Further, the size of proximal connectors used with shocking leads is typically different than the size of proximal connectors used with sensing/pacing leads. Hence, in order to connect the different sized proximal connectors to a system analyzer (or equivalent testing device) during the implant procedure, it has heretofore been necessary to use a plurality of cables, connector blocks, and/or a plurality of lead adapters for each size or type of proximal connector that may be encountered.

Connection of implanted stimulation leads to a system analyzer in the prior art typically consists of two sets of cables and connector blocks; one for shocking and one for pacing functions. Each connector block of the prior art typically includes two female connectors to which two corresponding proximal male connectors of the implanted stimulation leads may be temporarily attached. Such temporary attachment is typically achieved by using setscrew connectors mounted to the connector block that receive and grip the male tips of the implanted leads. A cable, usually hard-wired to the connectors at one end and having a multi-pin connector at the other end, then provides the appropriate electrical interface between the connectors and the system analyzer. Unfortunately, the connectors used on such adapters are still size-dependent (i.e., there is no single female connector to which all sizes of proximal lead male connectors can be safely connected). Hence, different lead adapters must still be used for different sized leads. Thus, a substantial inventory of lead adapters must be maintained for use in the operating room where the implant procedure is being carried out. Further, any such adapters which are used must be sterile, which requires a separate sterilizing operation. Moreover, the use of such adapters increases the risk of damage and/or connection error. That is, the frequent connecting and disconnecting of the proximal connectors to and from the setscrew or other female connectors of the lead adapters, can, if not carefully carried out, damage the proximal connectors, particularly the delicate proximal ring electrode, thereby rendering the implanted lead unsuitable. Further, there is always the chance when leads are frequently disconnected and re-connected that an error will occur in the polarity of the connections that are made.

Hence, there is a need in the art for a way to safely and efficiently connect the various sizes and types of proximal connectors existing on implanted stimulation leads to a system analyzer (or other testing device) used during the implant procedure. In short, there is a need for a universal connector that can be used with all implanted leads.

Further, it is desirable to test the performance of the implantable stimulation device prior to finalizing its implantation, i.e., prior to sewing up the patient at the conclusion of the implant operation. When the implantable stimulation device is an ICD, it is preferable that the ICD be connected to the implanted leads at the same time that the system analyzer is connected to the ICD in order to monitor its performance, particularly to monitor the output energy delivered by the ICD. Typically, the state-of-the-art requires that such output energy monitoring can only be accomplished by using some sort of in-line lead adapter, e.g., a "Y" adapter that connects the output of the ICD to both the implanted shocking leads and to the system analyzer. The use of such adapter, which must be sterile, requires additional connecting and disconnecting of the implanted lead, which additional connecting and disconnecting may further damage the proximal male connector of the lead or the corresponding female connector of the ICD. Further, such additional connecting also increases the possibility that a connection of the incorrect polarity will be made. A connection of the improper polarity could, where large shocking energies are used by an ICD, easily damage the system analyzer and/or the ICD, and could be harmful to the patient.

What is clearly needed, therefore, is a way to easily and safely test the performance of the ICD, including testing the output energy delivered by the ICD, after the shocking leads have been implanted and connected to the ICD. Accompanying this need is the need to perform such testing without the use of any special adapters that require additional disconnecting of the leads from the ICD and without the possibility of making a mistake in the polarity of the connection.

Thus, in summary, to minimize the risk of lead damage or polarity connection error, what is needed is an implant procedure or technique wherein the implanted leads may be detachably connected to the system analyzer without using adapters or other holding mechanisms that could damage the leads; and wherein once the leads have been tested by the system analyzer, the leads may be connected to the ICD (or other stimulation device) just once, yet that still allows the ICD to be fully tested after the leads have been so connected, including the testing of the output energy delivered by the ICD, without concern for whether a proper polarity has been achieved between the ICD and the system analyzer.

In one known instance, an ICD clamp assembly is designed to be used with the cable connector block that permits an in-line electrical connection of the proper polarity to be established between the ICD and the cable connector block after the implanted leads have been connected to the ICD. Advantageously, the ICD clamp assembly includes a clamp that simply clamps over the ICD and establishes electrical contact with the setscrews or other securing means used to secure the proximal terminal of the shocking leads to the ICD, thereby providing the desired in-line electrical connection without the use of any adapters that require the disconnecting of the shocking leads from the ICD. Moreover, the clamp is specially configured so that it can only clamp over the ICD and make contact with the shocking lead setscrews in one orientation, thereby assuring that the resulting electrical connection is of the proper polarity. The clamp connector of the clamp assembly is electrically connected to the connector block through a cable and keyed plug, thereby further assuring that the proper polarity is maintained at the cable connector block. Hence, by simply clamping the clamp over the ICD, plugging the keyed plug of the clamp assembly into the cable connector block, and connecting the cable connector block to the system analyzer, the system analyzer can monitor the performance of the ICD including the output energy delivered by the ICD without concern for whether a proper polarity connection has been established between the ICD and the system analyzer.

However, with the introduction of a relatively recent standard known as IS-4 (officially "active implantable medical devices—four-pole connector system for implantable cardiac rhythm management devices") calls for seals to be placed in the connector cavity and not on the lead connector, known techniques of connection have had to be reconsidered. Specifically, with the development of the new IS-4 or similar lead wires, alligator clips and the like can no longer be used because the ring contacts are too close to each other and may cause electrical shorting.

It was in light of the foregoing that the present invention was conceived and has now been reduced to practice.

SUMMARY

A universal cable connector for detachably connecting a stimulation lead to a system analyzer includes a nonconductive connector block for releasably receiving and holding fixed a proximal end of the lead including at least one proximate contact electrically in continuity with a distal electrode at the distal end of the lead, a system analyzer cable for selectively electrically interconnecting an associated proximate contact and the system analyzer, and a switch mechanism for selectively connecting electrically the system analyzer cable with the proximate contact thereby enabling the system analyzer to determine the efficacy of the chosen body tissue site. The connector block includes a nest region for receiving the proximal end of the lead and the switch mechanism includes a switch contact electrically engaged with the system analyzer cable and movable between a first position disengaged from an associated and selected exposed proximate contact and a second position engaged with the proximate contact for electrically connecting the distal electrode via each of the associated and selected ones of the proximate contacts to the system analyzer.

As noted earlier, historically, pacemakers, ICDs, or other similar devices have used lead wires that connect directly to the heart and are located in very specific areas. In order for an attending physician to verify that the lead wires have achieved an acceptable contact, the use of a patient system analyzer (PSA) is needed. The interface mechanism has been a cable set utilizing a connector that plugs into the PSA at the proximal end and at the distal end a set of alligator clips is used. The invention is directed towards a cable mechanism that eliminates the need for the alligator clips. In this regard, a cable including a clamp with metal contacts is placed over the IS-4 lead, then, in one embodiment, a series of switch levers will allow the doctor to select the combination of connections desired. In another embodiment, there are different connectors with predetermined connections to be selectively made.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 2A is a detail side elevation view of a proximate low-voltage connector of an industry standard IS-4 lead for addressing Bradycardia syndrome;

FIG. 2B is a detail side elevation view of a combined high and low-voltage proximate connector a combined high and low-voltage proximate connector for addressing Tachycardia syndrome;

FIG. 3 is a chart to relate information about the construction and operation of the leads illustrated in FIGS. 1 and 2;

DETAILED DESCRIPTION OF THE PREFERRED EMBODIMENT

Figure 1:
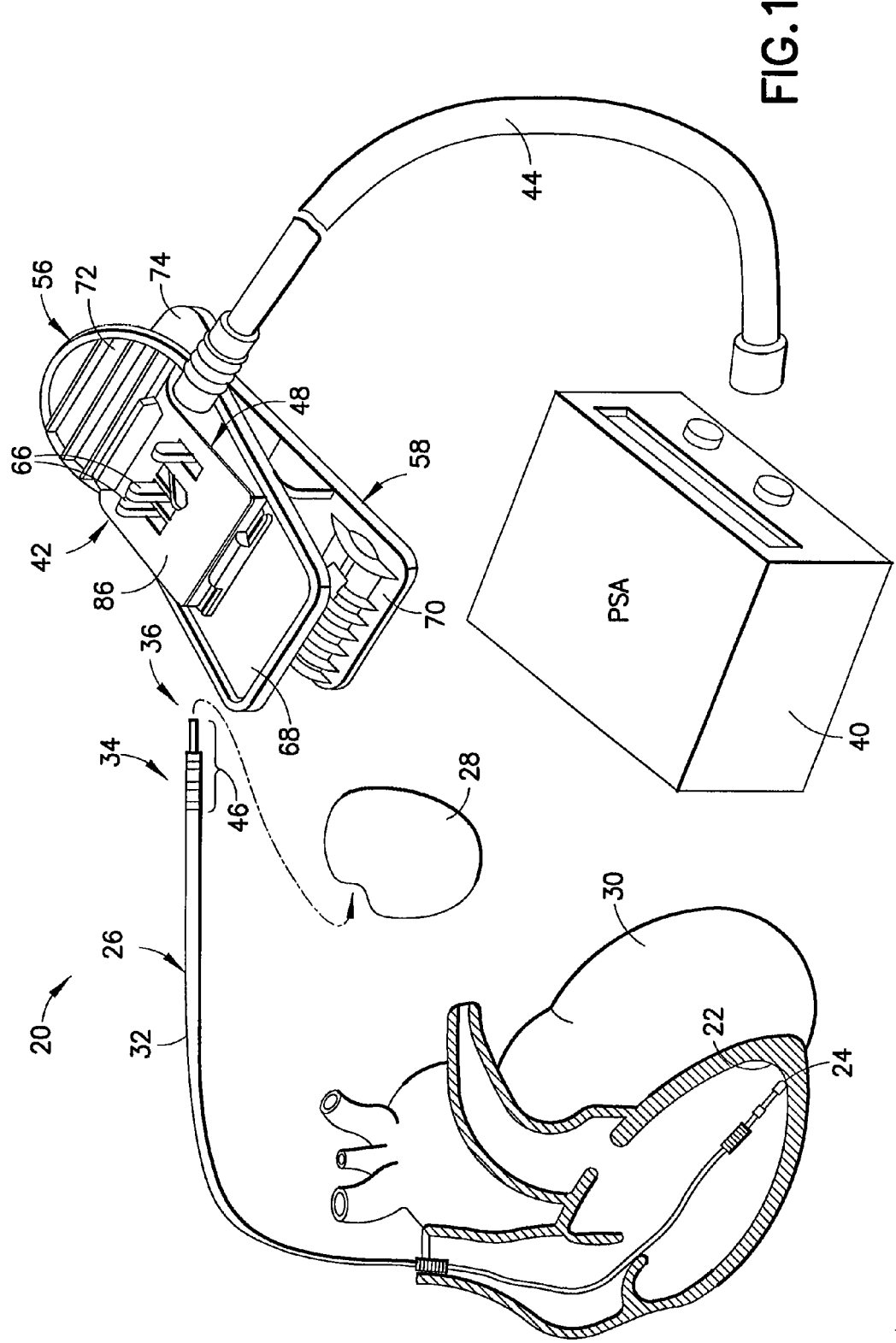
FIG. 1 is a diagrammatic perspective view illustrating a system embodying the present invention for testing a lead intended to be connected to an electrical heart stimulator device.
Figure 4:
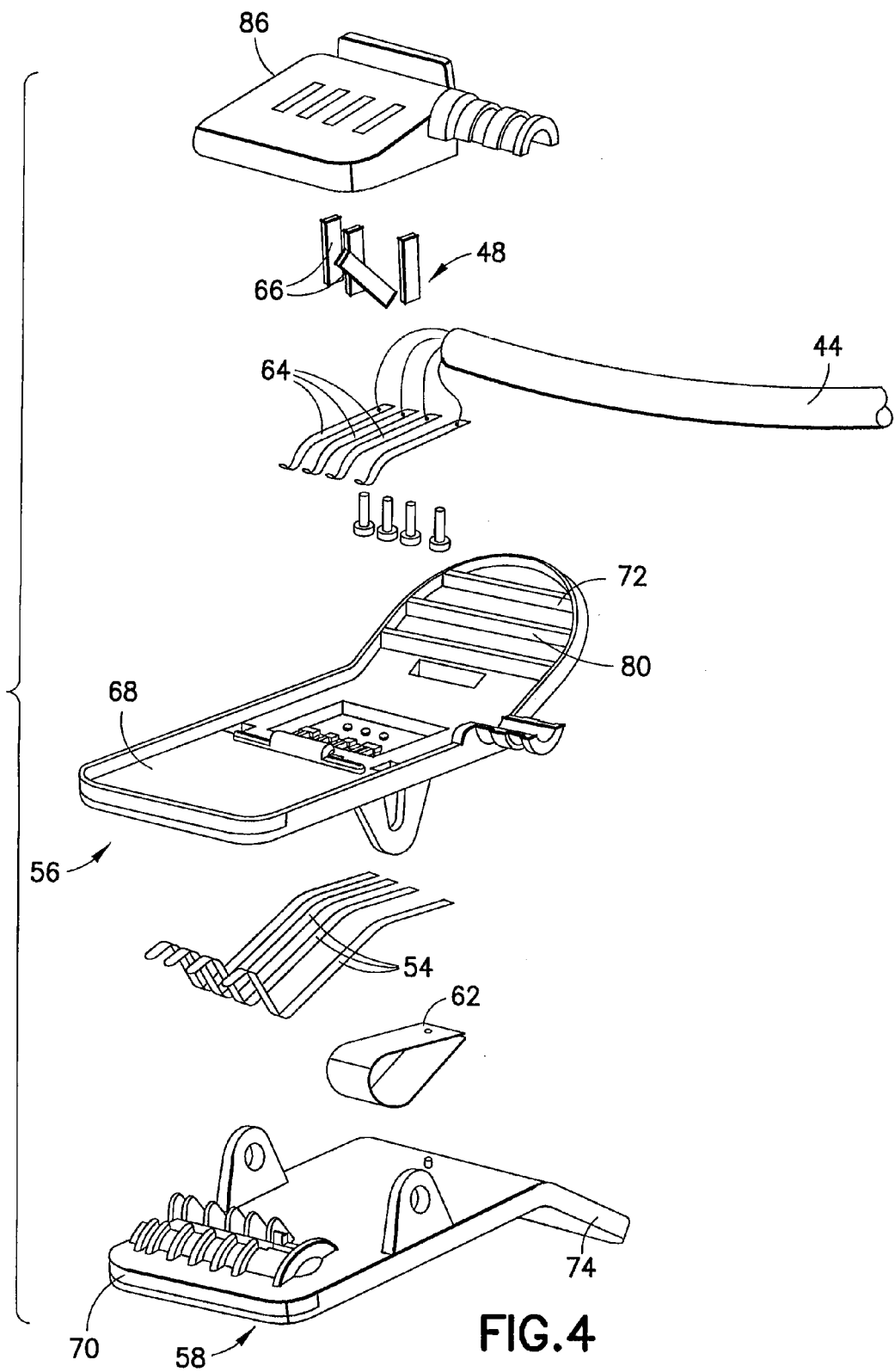
FIG. 4 is an exploded perspective view of a universal cable connector illustrated as a component of the system shown in FIG. 1 and embodying the present invention.
Figure 5:
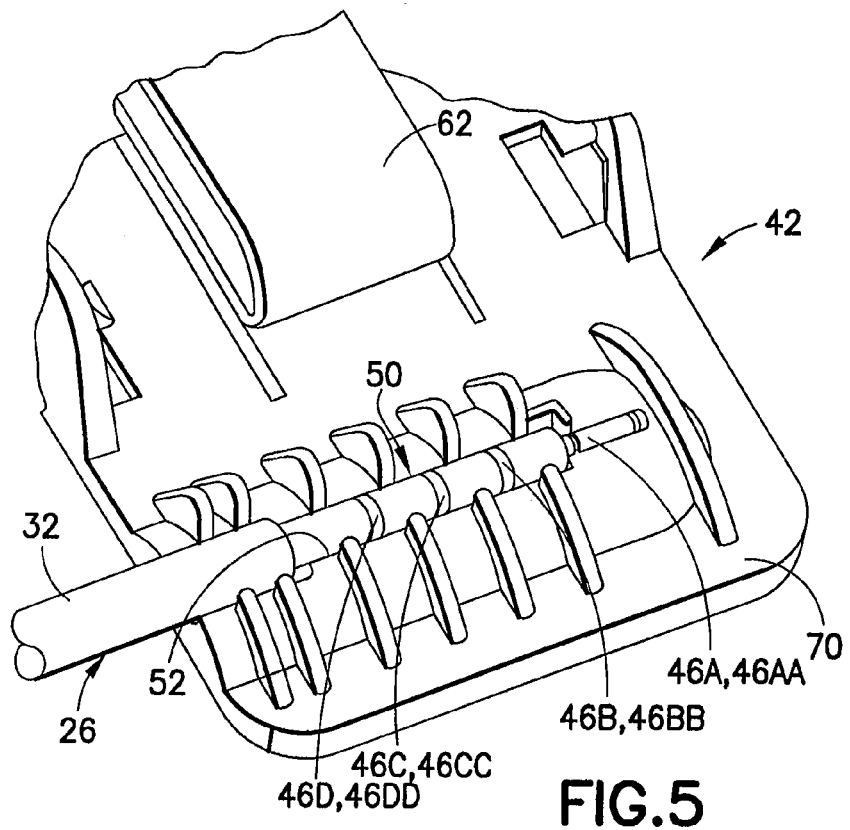
FIG. 5 is a detail perspective view of parts illustrated in FIG. 4.
Figure 6:
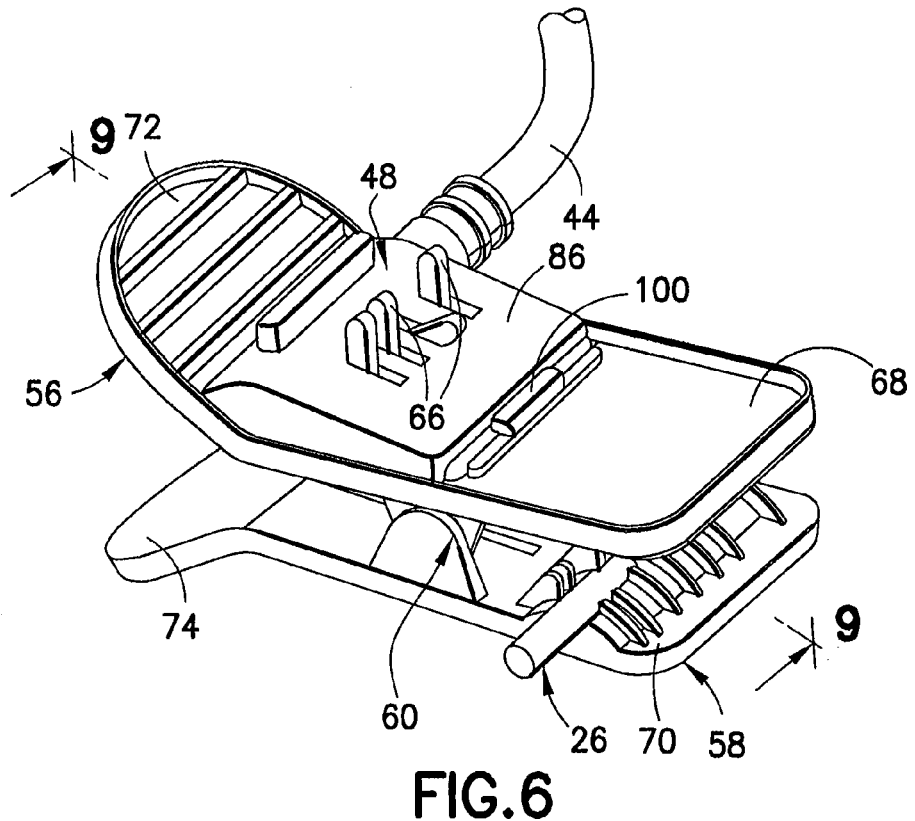
FIG. 6 is a perspective view of the universal cable connector illustrated in FIG. 4 in its assembled condition.
Figure 7:
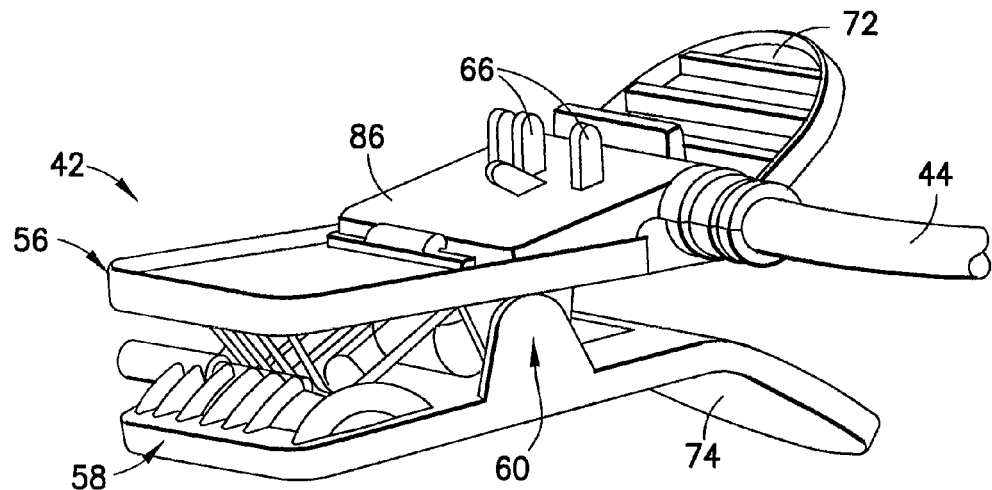
FIG. 7 is another perspective of the universal cable connector illustrated in FIG. 4 in its assembled condition.

Refer now to the drawings and, initially, to FIG. 1 which illustrates a system 20 for determining the efficacy of a body tissue site 22 chosen for an electrode 24 at a distal end of a lead 26 intended for connecting an implantable electrical stimulation device 28 to the body tissue. The system 20 incorporates features of the present invention for use in association with the stimulation device 28 such as a pacemaker or cardioverter-defibrillator (ICD) providing electrical stimulation to a heart 30. Although the present invention will be described with reference to the embodiments shown in the drawings, it should be understood that the present invention can be embodied in many alternate forms or embodiments. In addition, any suitable size, shape or type of elements or materials could be used. The lead 26 includes an insulating sheath 32 interconnecting the electrode 24 appropriately secured to the interior wall of the heart at the body tissue site 22 and an electrical connector 34 at a proximal end 36 to which can be attached the electrical stimulation device 28.

As earlier noted, it is necessary for the attending physician to verify that the body tissue site selected for the implantation procedure is appropriate and will provide the desired result. For this reason, a PSA (patient system analyzer) 40 is an integral component of the system 20. in short, the PSA 40 is an external testing and measuring device which, for example, can pace the heart during the implantation procedure and can measure stimulation thresholds, sensing thresholds, and lead impedance. The PSA 40 may also be used to test pulse generator function prior to implant, measure slew rate or print an electrogram of a sensed R-wave.

Figure 8:
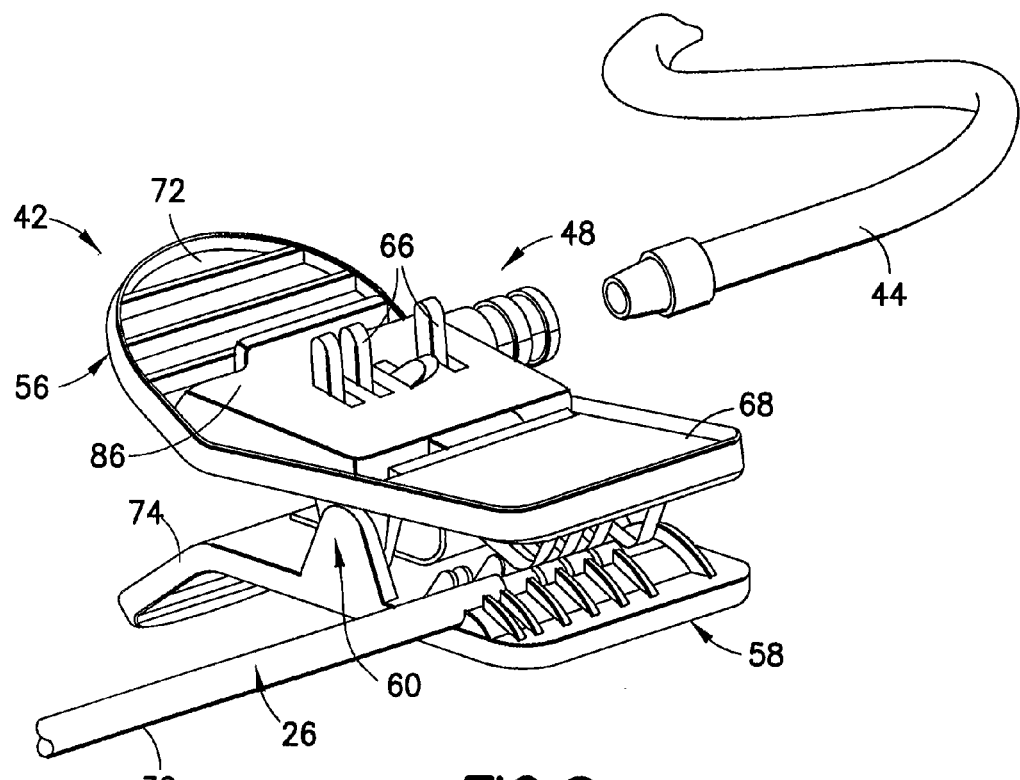
FIG. 8 is still another perspective of the universal cable connector illustrated in FIG. 4 in its assembled condition.

In order to use the PSA 40 in connection with the lead 26, it is necessary to connect the electrical connector 34 of the lead 26 to the PSA. To achieve this result, a nonconductive connector block 42 is provided for releasably receiving and holding fixed the proximal end 36 of the lead 26. The connector block 42 is composed of sterilizable materials, polyvinyl chloride being one acceptable material, and may be so inexpensively made as to be disposable. A system analyzer cable 44 which may be detachable from the connector block 42 (see FIG. 8) serves to electrically interconnect proximate contacts collectively indicated by reference numeral 46 and the PSA 40 and a plurality of switch mechanisms 48 serve to selectively connect electrically the system analyzer cable with the proximate contacts so that, as noted earlier, the PSA can determine the efficacy of the chosen body tissue site 22.

A relatively recent international standard designation for lead connector designs is known as IS-4 (officially "Active implantable medical devices—four-pole connector system for implantable cardiac rhythm management devices") calls for seals to be placed in the connector cavity and not on the lead connector. Its purpose is to specify a standard connector assembly to provide interchangeability between specific implantable leads and specific implantable stimulation devices from different manufacturers. The standard has been devised to allow for a reduction in the number of individual lead connectors, reduced pocket bulk associated with earlier existing bifurcated or trifurcated leads, reduced interaction of the lead bodies in the pocket, and reduction or elimination of setscrew connections. One version as illustrated in FIG. 2A is a low-voltage connector 34A for addressing Bradycardia syndrome and another version as illustrated in FIG. 2B is a combined high and low-voltage connector 34B addressing Tachycardia syndrome.

As seen in FIG. 2A, the Bradycardia connector 34A includes a plurality of proximate contacts, namely, a straight pin tip contact 46A, and three ring contacts 46B, 46C, and 46D, respectfully, as one advances in a distal direction. Each of the contacts 46A, 46B, 46C, and 46D is of a low voltage design and is separated from its neighbor by a sealing surface 50. In this instance, the lead is designated 26A and the insulating sheath is designated 32A. Similarly, as seen in FIG. 2B, the Tachycardia connector 34B includes a plurality of proximate contacts, namely, a stepped pin tip contact 46AA, and three ring contacts 46BB, 46CC, and 46DD, respectfully, as one advances in a distal direction. The contacts 46AA and 46BB are of low voltage design and each contact is separated from its neighbor by a sealing surface 50 while the contacts 46CC and 46DD are of high voltage design and are similarly separated from their neighbors by sealing surfaces 50. In this instance, the lead is designated 26B and the insulating sheath is designated 32B. The particular information obtained from each contact depends on the lead placement and the information being sought by the physician. This data is used to interpret the condition of the patient's heart. The contact assignment is shown in tabular format in FIG. 3.

Turn now to FIGS. 4-8 for a more specific description of the connector block 42. The connector block 42 includes a grooved or channel-like nest region 52 (see especially FIG. 5) for receiving the proximal end 36 of the lead 26. Especially viewing FIGS. 9 and 10, each switch mechanism 48 includes a switch contact 54 electrically engaged with the system analyzer cable 44 (FIGS. 1, 4, 6, 7, and 8) and movable between a first position (FIG. 9) disengaged from an associated and selected one of the exposed proximate contacts 46 and a second position (FIG. 10) engaged with an associated and selected one of the proximate contacts 46 for electrically connecting the distal electrode 24 via each of the associated and selected ones of the proximate contacts to the system analyzer PSA 40.

Figure 9:
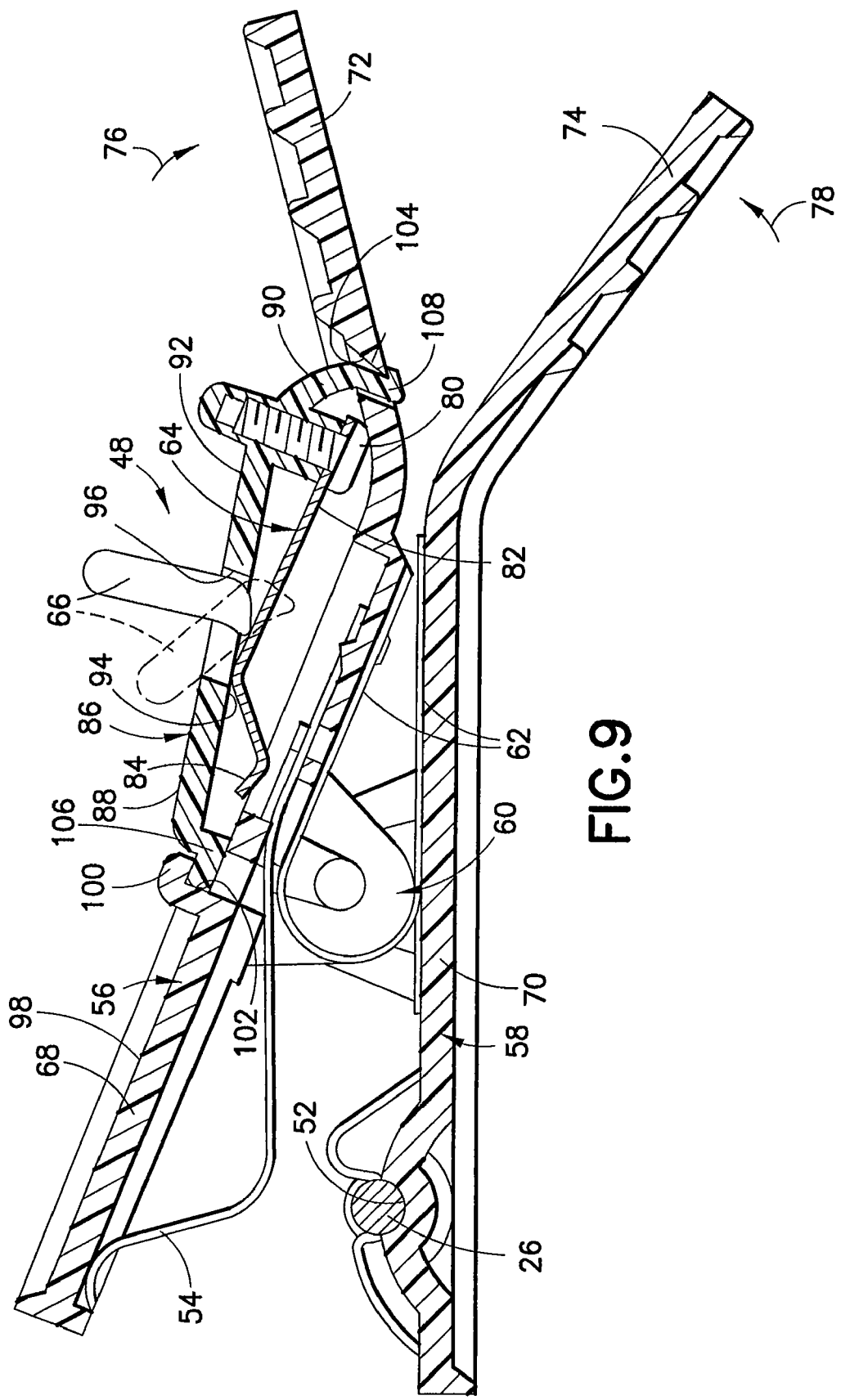
FIG. 9 is an elevation cross section view taken generally along line 9-9 in FIG. 6 and depicting parts in the raised position.
Figure 10:
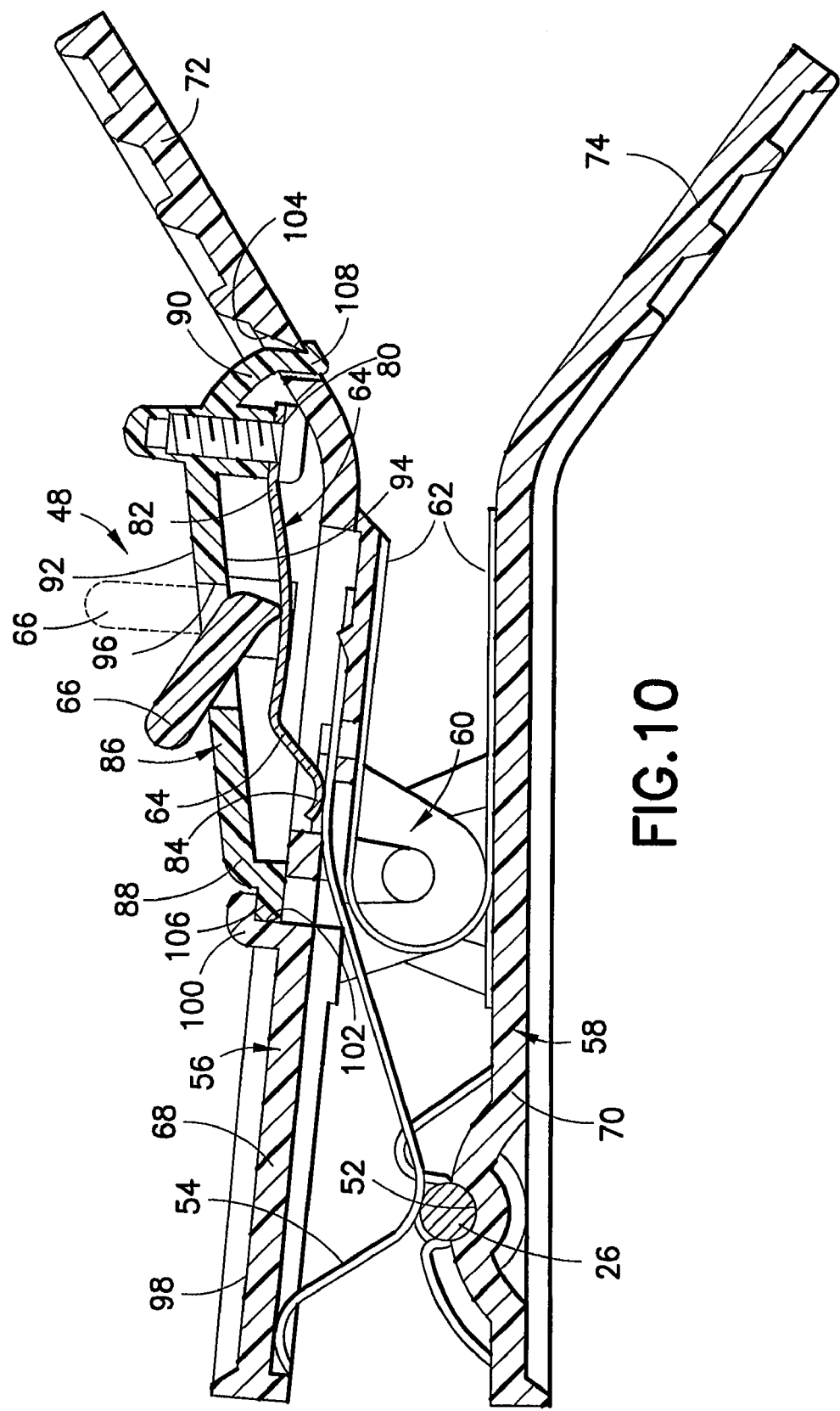
FIG. 10 is another cross section view, similar to FIG. 9 and depicting parts in the lowered position.
Figure 11:
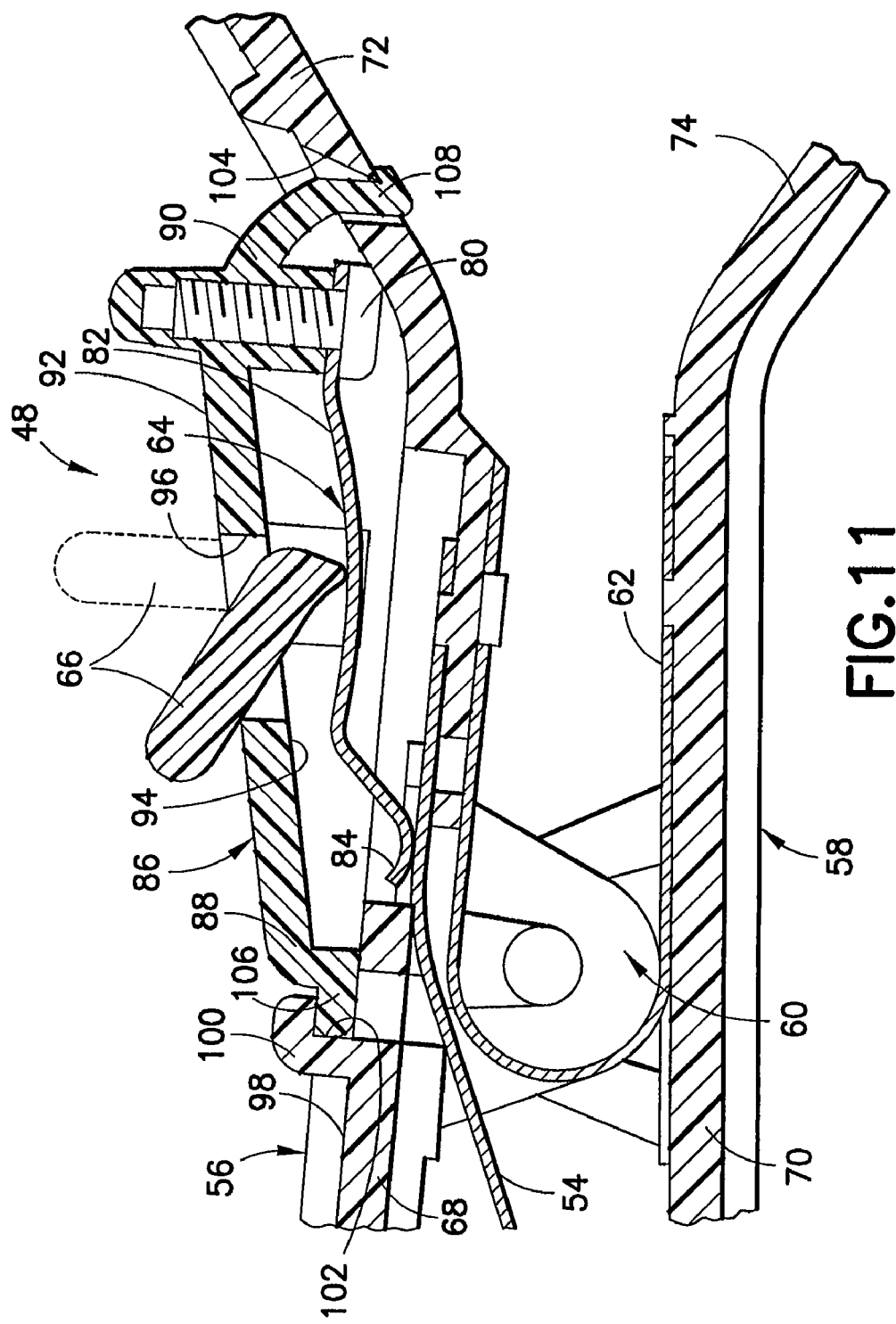
FIG. 11 is a detail cross section view to illustrate more clearly parts shown in FIGS. 9 and 10.
Figure 11A:
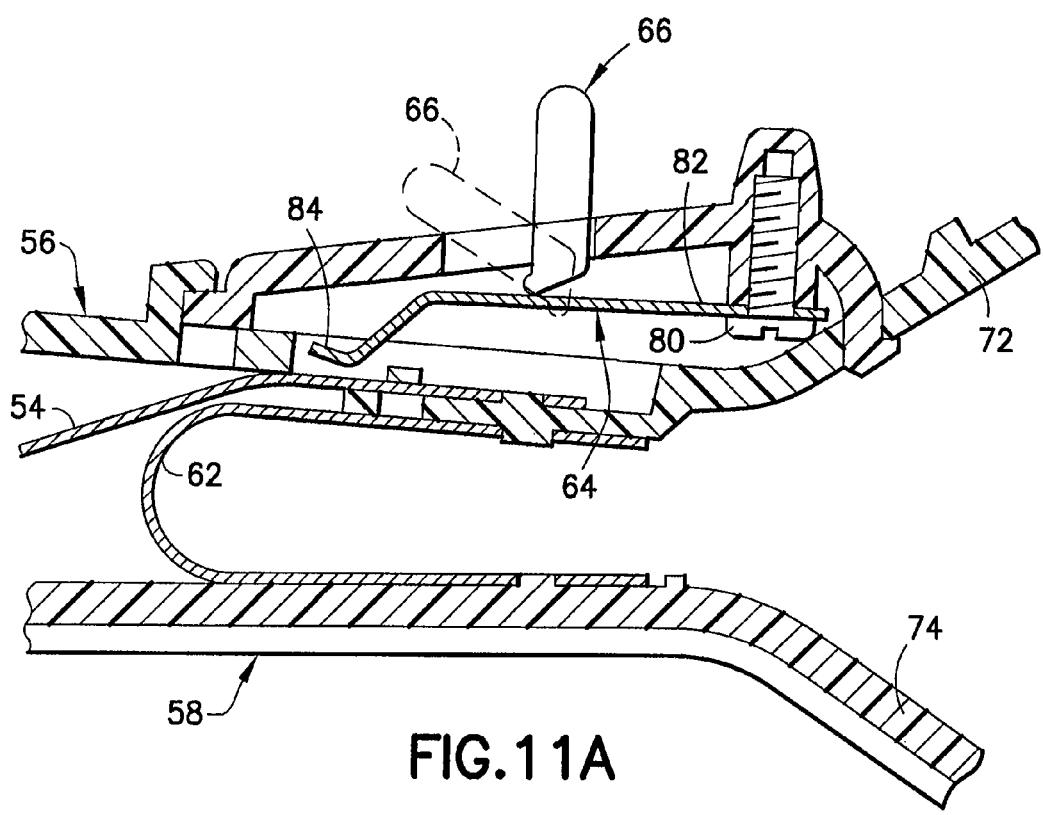
FIG. 11A is an even more detailed cross section view of a portion of FIG. 9.

Continuing in this regard, the connector block 42 includes an upper housing 56, a lower housing 58 with the nest region 52 for receiving the proximal end 36 of the lead 26, and a hinge mechanism 60 pivotally mounting the upper housing and the lower housing for relative movement between a raised position (FIG. 9) and a lowered position (FIG. 10). In the raised position, the upper housing 56 is distant from the nest region 52 and in the lowered position (FIG. 10), the upper housing is proximate the nest region. A flat spring 62 biases the upper housing 56 toward the lowered position. A switch contact 54 mounted on the upper housing 56 is engaged with an associated exposed proximate contact 46 of the lead 26 when the upper housing is in the lowered position. A pivotally mounted switch handle 66 is movably engageable with each associated housing contact 64 for movement of the associated housing contact between a first solid line position (FIGS. 9 and 11A) at which the associated housing contact 64 is disengaged from the associated switch contact 54 and a second dashed line position (FIGS. 10 and 11) at which the associated housing contact is engaged with the switch contact 54 thereby completing the electrical connection between the distal electrode 24 and the PSA 40.

Continuing to view FIGS. 9 and 10, it can be readily seen that the upper and lower housings 56, 58, respectively, are substantially co-terminous, each including a front planar element 68, 70, respectively, and a rear planar element 72, 74, respectively. The front planar elements 68, 70 of the upper and lower housings 56, 58 lie in planes which subtend a minor acute angle. The rear planar elements 72, 74 of the upper and lower housings 56, 58 lie in planes which subtend a major acute angle which is greater than the minor acute angle between the front planar elements 68, 70. With this construction, opposed forces indicated in FIG. 9, respectively, by arrows 76, 78 imposed on the rear planar elements 72, 74 towards one another operate to move the upper and lower housings to relative raised positions as seen in FIG. 10.

A unique junction 80 electrically connects each housing contact 64 and the system analyzer cable 44. Each housing contact 64 has a passive end 82 connected to the unique junction 80 and a free active end 84 distant from the passive end engaged with each associated switch contact 54 when the switch handle is in the second position and disengaged from each associated switch contact when the switch handle is in the first position.

A cover 86 overlies the upper housing 56 and extends between forward and aft spaced apart transversely extending attachment members 88, 90, respectively. Viewing now especially FIG. 11, the cover 86 has an upper surface 92 and a lower surface 94 and a through opening 96 intermediate the forward and aft attachment members 88,90. The upper housing 56 has an upper surface 98 and a transversely extending flange 100 projects above the upper surface and defines a transverse recess 102 and, spaced from the flange member, is a transversely extending slot 104. The forward attachment member 88 includes a straight edge member 106 which is receivable in the recess 102. In a somewhat similar manner, the aft attachment member 90 includes a barbed edge member 108 which is slidably, then lockingly, received in the transversely extending slot 104. Each switch handle 66 is pivotally mounted on the cover 86 beneath the lower surface 94 and projects through the opening 96 to a location above the upper surface 92. As earlier noted, the unique junction 80 is also mounted on the cover 86 and electrically connects each housing contact 64 and the system analyzer cable 44.

In operating the system 20 with the connector block 42, the proximal end 36 of the lead 26 is placed in the nest region 52 of the lower housing 58 in the manner especially well illustrated in FIGS. 5-10. In order for this to occur, viewing FIG. 9, the operator must take hold of the connector block and apply force on the rear planar elements 72, 74 in the directions indicated by arrows 76, 78, respectively. With this operation, the upper housing is moved against the bias of flat spring 62 away from lower housing 58 (away from the position illustrated in FIG. 10 and toward the position illustrated in FIG. 9) thereby enabling the proximal end 36 of the lead 26 to be placed in the nest region 52. The operator then releases the force previously applied on the rear planar elements 72, 74 and, under the bias of spring 62, the connector block is returned to the position of FIG. 10. In this position, each switch contact 54 engages an associated one of the proximate contacts 46 of the lead 26 and, under the force of the spring 62, the proximal end 36 of the lead is held firmly in place until such time that it is desired to remove the lead by again moving the upper housing 56 away from lower housing 58.

With the proximal end 36 of the lead held firmly in place in the nest region, the switch handles 66 can be operated in any desired combination to connect any combination of the proximate contacts to PSA 40.

The preceding description relates the construction and operation of a preferred embodiment of the invention. However, it may be desirable in certain instances to employ a modified connector block which is of simpler design absent the switch mechanism 48 and absent the components necessary for the operation of the switch mechanism. For purposes of the description of this modified connector block, 200-series reference numerals will be used with the tens-digits numerals being used to indicate the components which are unchanged from the earlier embodiment.

Figure 12:
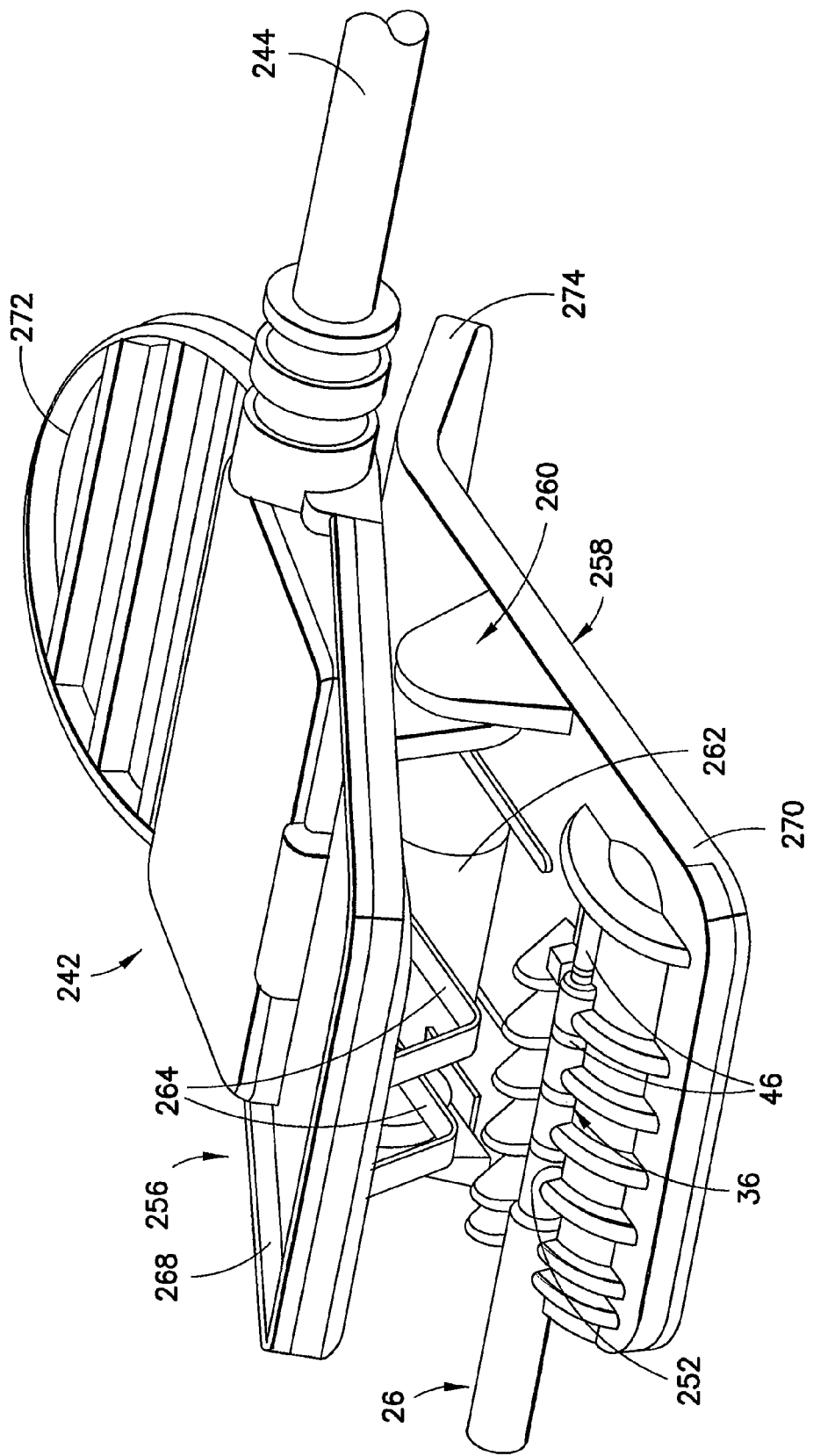
FIG. 12 is a detail perspective view of another embodiment of the universal cable connector of the invention and depicting one particular configuration thereof.
Figure 13:
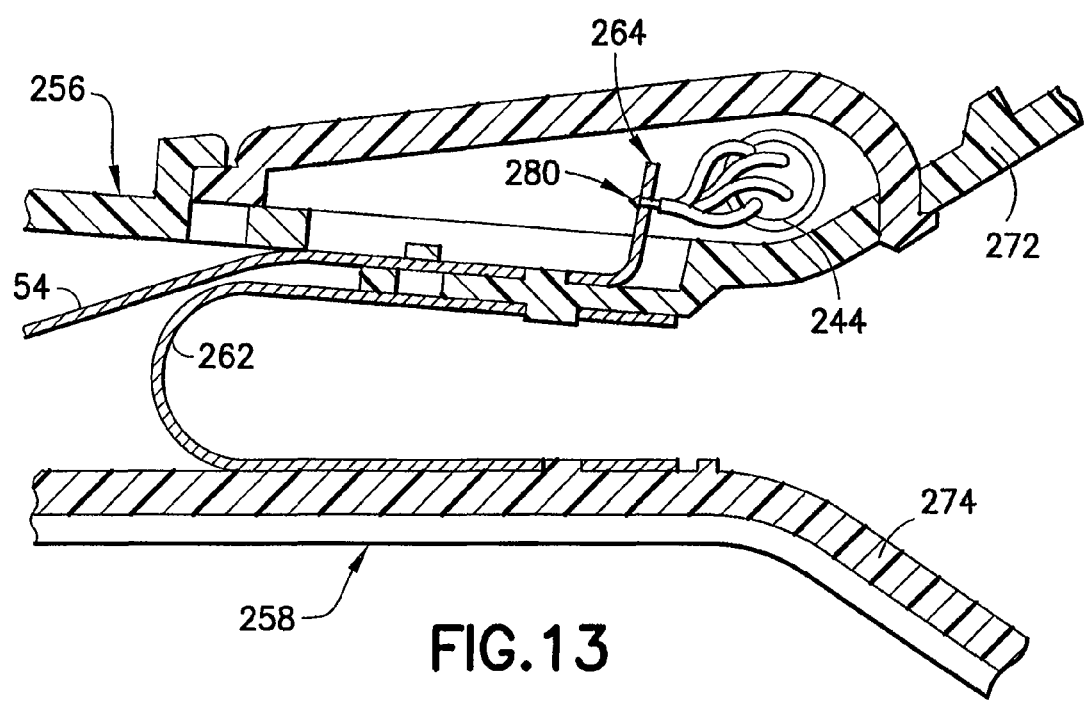
FIG. 13 is a cross-sectional side view of one embodiment of the universal cable connector.

Turn now to FIGS. 12 and 13. A nonconductive connector block 242 releasably receives and holds fixed, as in the earlier-described embodiment, a proximal end 36 of a lead 26 including at least one proximate contact 46, and likely a plurality of the proximate contacts, electrically in continuity with the electrode 24 at the distal end of the lead (FIG. 1).

The connector block 242 includes a nest region 252 for receiving the proximal end 36 of the lead 26, an upper housing 256, a lower housing 258 formed with the nest region, a hinge mechanism 260 pivotally mounting the upper housing and the lower housing for relative movement between a raised position at which the upper housing is distant from the nest region and a lowered position at which the upper housing is proximate the nest region. A flat spring 262 biases the upper housing toward the lowered position and at least one housing contact 264 is mounted on the upper housing engaged with an associated exposed proximate contact 46 of the lead 26 when the upper housing 256 is in the lowered position.

The upper and lower housings 256, 258 are substantially co-terminous, each including a front planar element 268, 270, respectively, and a rear planar element 272, the front planar elements of the upper and lower housings lying in planes which subtend a minor acute angle, the rear planar elements of the upper and lower housings lying in planes which subtend a major acute angle which is greater than the minor acute angle. A unique junction 280 on the upper housing 256 electrically connects each housing contact 264 and the system analyzer cable 244. Each housing contact 264 has a passive end 282 connected to the unique junction 280 and an active end 284 distant from the passive end engaged with each associated housing contact when the upper housing is in the second position (like FIG. 10 of the earlier embodiment) and disengaged from each associated switch contact when the upper housing is in the first position (like FIG. 9 of the earlier embodiment).

In operating the system with the connector block 242, the proximal end 36 of the lead 26 is placed in the nest region 252 of the lower housing 258 in the manner especially well illustrated in FIG. 12. In order for this to occur, viewing FIG. 9 of the previous embodiment, the operator must take hold of the connector block and apply force on the rear planar elements 272, 274 toward one another. With this operation, the upper housing 256 is moved against the bias of flat spring 262 away from lower housing 258 thereby enabling the proximal end 36 of the lead 26 to be placed in the nest region 252. The operator then releases the force previously applied on the rear planar elements 272, 274 and, under the bias of spring 262, the connector block 242 is returned to the position at which each housing contact 264 engages an associated one of the proximate contacts 46 of the lead 26 and, under the force of the spring 262, the proximal end 36 of the lead is held firmly in place until such time that it is desired to remove the lead by again moving the upper housing 256 away from lower housing 258.

With the proximal end 36 of the lead 26 held firmly in place in the nest region 252, the housing contacts 264 therein illustrated are positioned to engage an appropriate one or ones of the proximate contacts 46. Viewing FIGS. 2A and 2B, let it be said that the proximate contacts 46A and 46AA are tip contacts, that proximate contacts 46B and 46BB are first ring contacts, that proximate contacts 46C and 46CC are second ring contacts, and that proximate contacts 46D and 46DD are third ring contacts, That being said, in FIG. 12, the housing contacts 264 are positioned to engage both first ring contact 46B or 46BB and third ring contact 46D or 46DD of the lead 26 and put them into electrical commonality with PSA 40. The connector block 242 has only the capability, then, of connecting the distal electrode 24 via either of first ring contacts 46B or 46BB and either of third ring contacts 46D or 46DD with PSA 40. Other combinations and permutations of this second embodiment of the invention are possible, and those will now be illustrated and discussed.

Figure 12A:
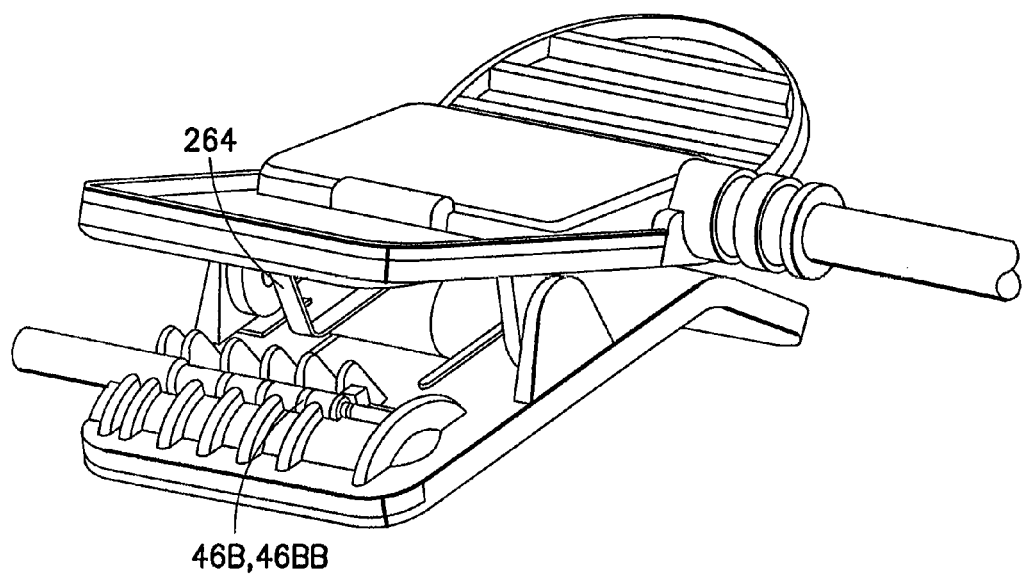
FIGS. 12A through 12N are detail perspective views of the other embodiment of the universal cable connector, similar to that illustrated in FIG. 12 but depicting various other particular configurations thereof.

In FIG. 12A, a single housing contact 264 is positioned to engage the first ring contact 46B or 46BB of the lead 26 and put it into electrical commonality with PSA 40.

Figure 12B:
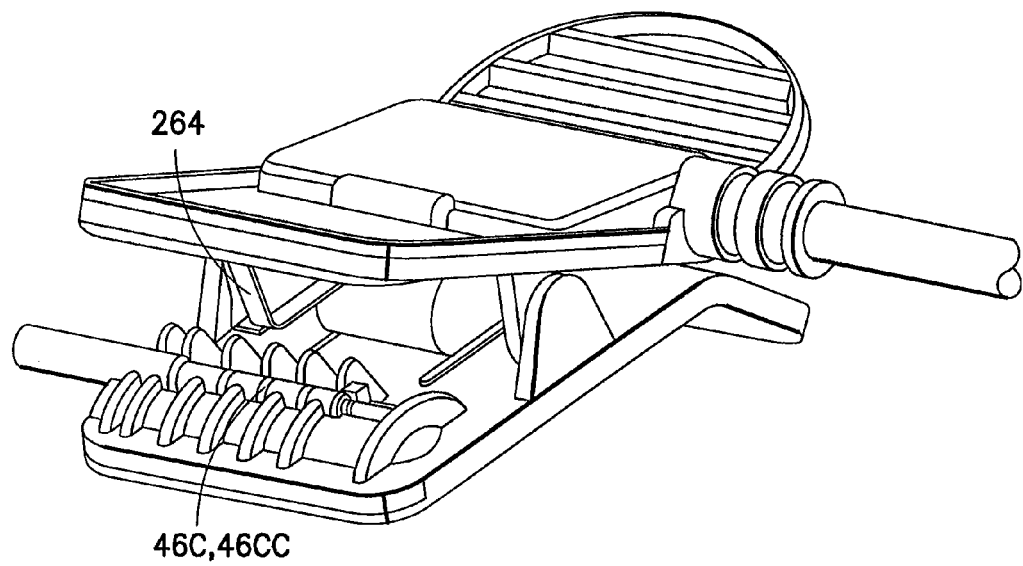

In FIG. 12B, a single housing contact 264 is positioned to engage the second ring contact 46C or 46CC of the lead 26 and put it into electrical commonality with PSA 40.

Figure 12C:
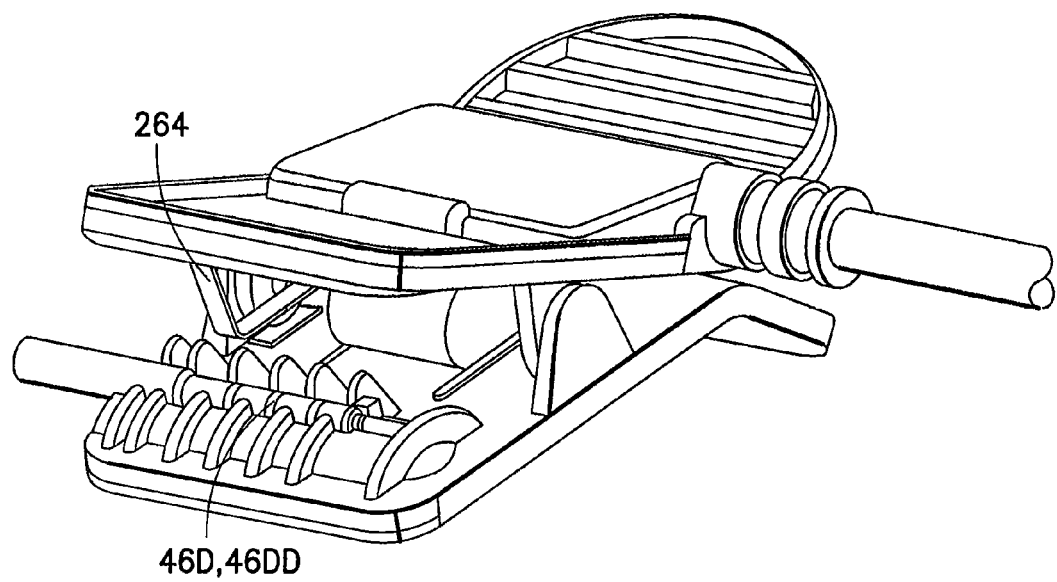

In FIG. 12C, a single housing contact 264 is positioned to engage the third ring contact 46D or 46DD of the lead 26 and put it into electrical commonality with PSA 40.

Figure 12D:
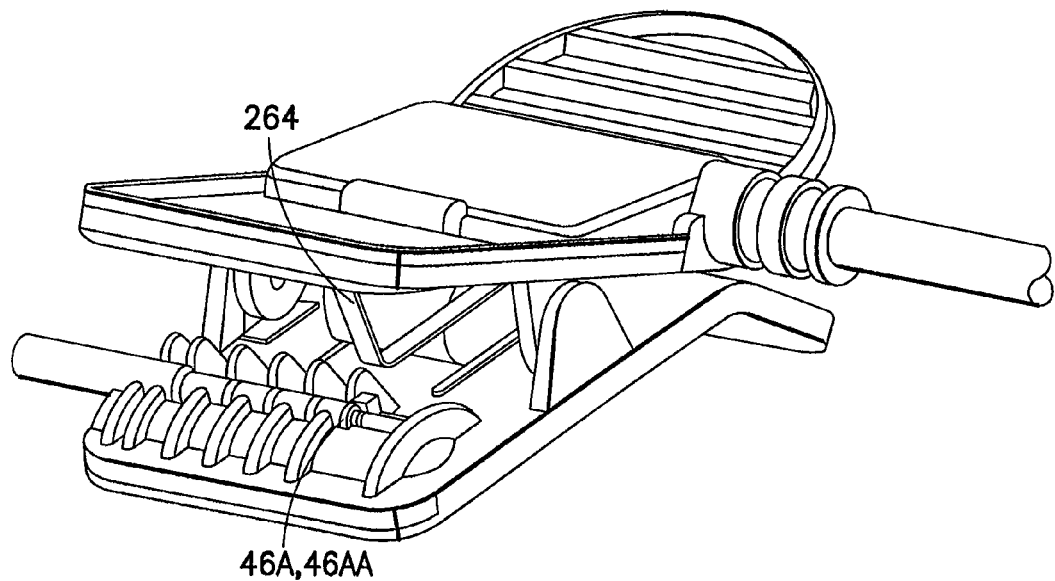

In FIG. 12D, a single housing contact 264 is positioned to engage the tip contact 46A or 46AA of the lead 26 and put it into electrical commonality with PSA 40.

Figure 12E:
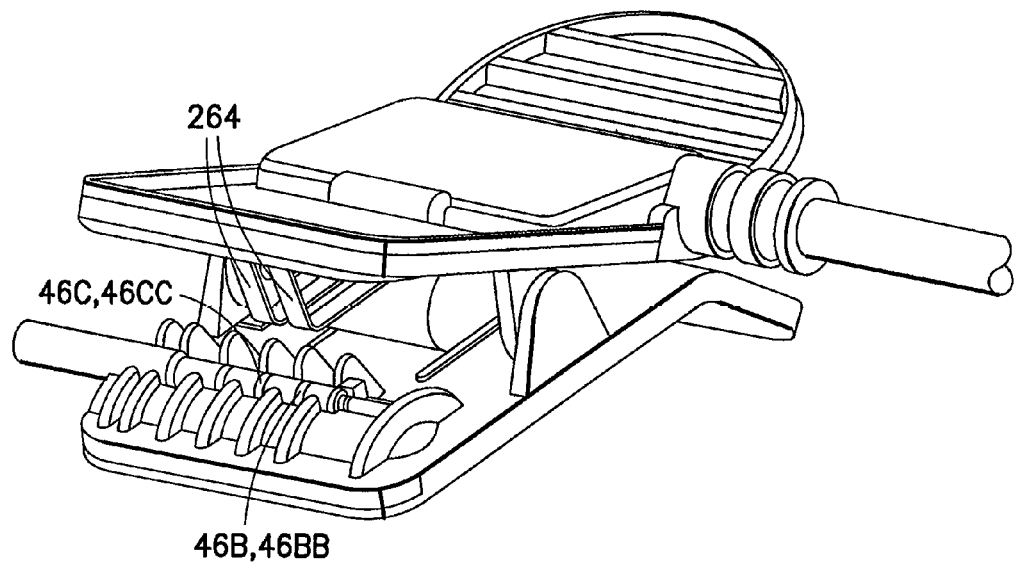

In FIG. 12E, the housing contacts 264 are positioned to engage both first ring contact 46B or 46BB and second ring contact 46C or 46CC of the lead 26 and put them into electrical commonality with PSA 40.

Figure 12F:
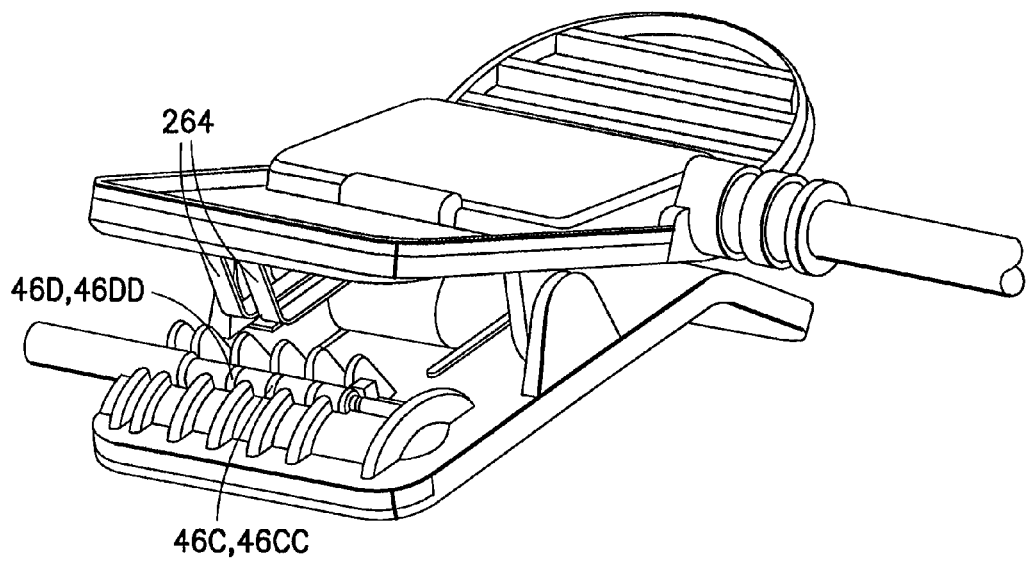

In FIG. 12F, the housing contacts 264 are positioned to engage both second ring contact 46C or 46CC and third ring contact 46D or 46DD of the lead 26 and put them into electrical commonality with PSA 40.

Figure 12G:
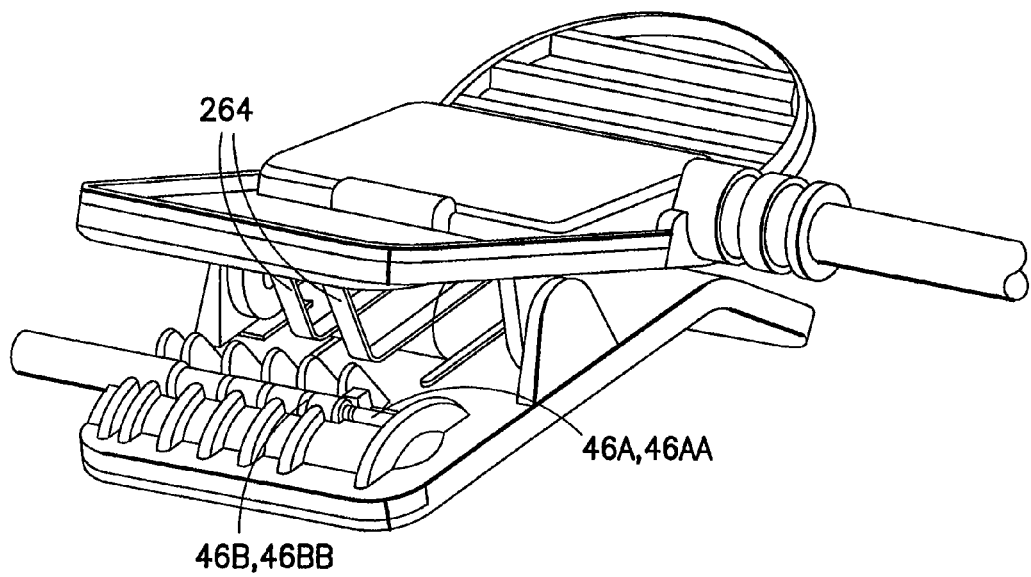

In FIG. 12G, the housing contacts 264 are positioned to engage both tip contact 46A or 46AA and first ring contact 46B or 46BB of the lead 26 and put them into electrical commonality with PSA 40.

Figure 12H:
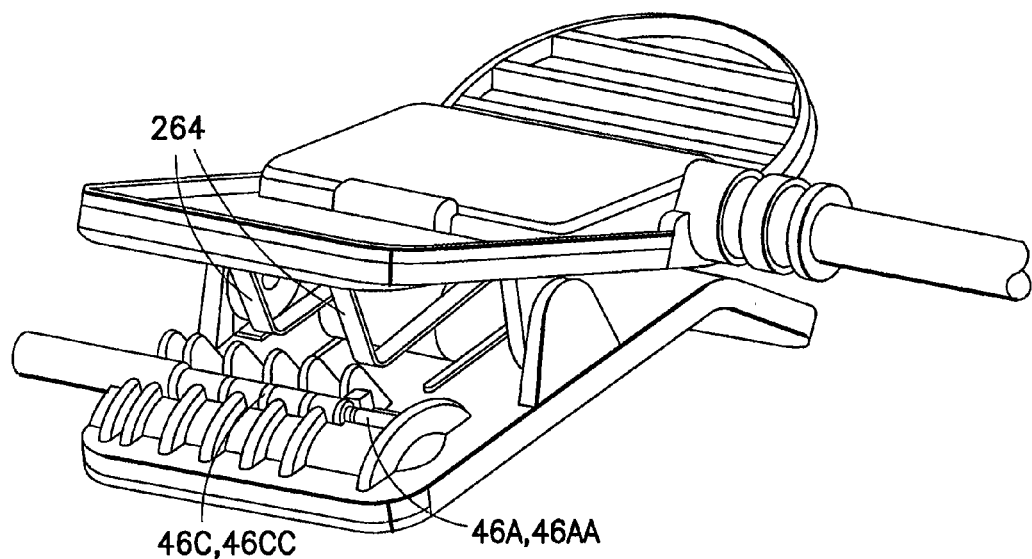

In FIG. 12H, the housing contacts 264 are positioned to engage both tip contact 46A or 46AA and second ring contact 46C or 46CC of the lead 26 and put them into electrical commonality with PSA 40.

Figure 12I:
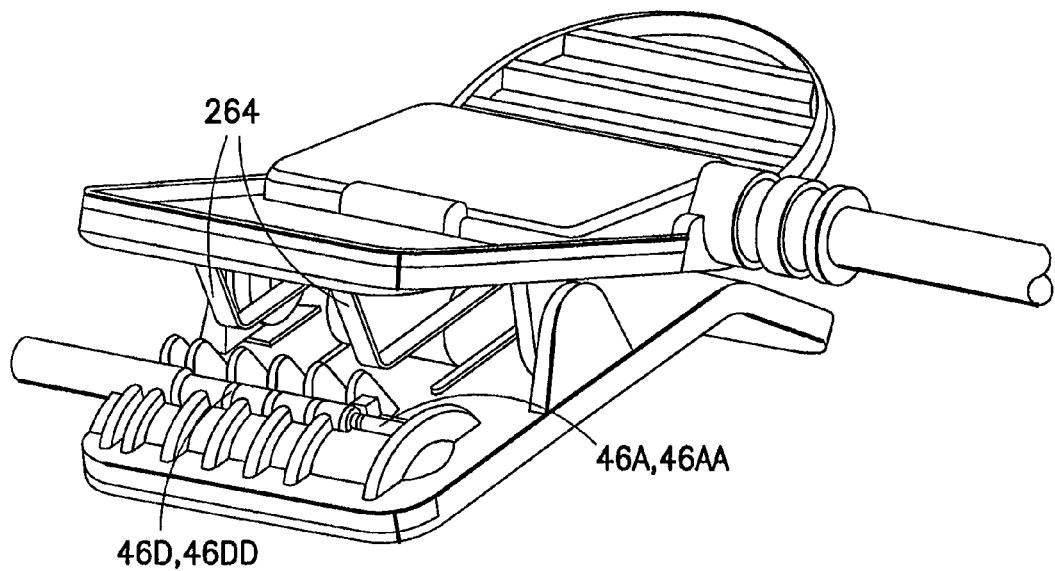

In FIG. 12I, the housing contacts 264 are positioned to engage both tip contact 46A or 46AA and third ring contact 46D or 46DD of the lead 26 and put them into electrical commonality with PSA 40.

Figure 12J:
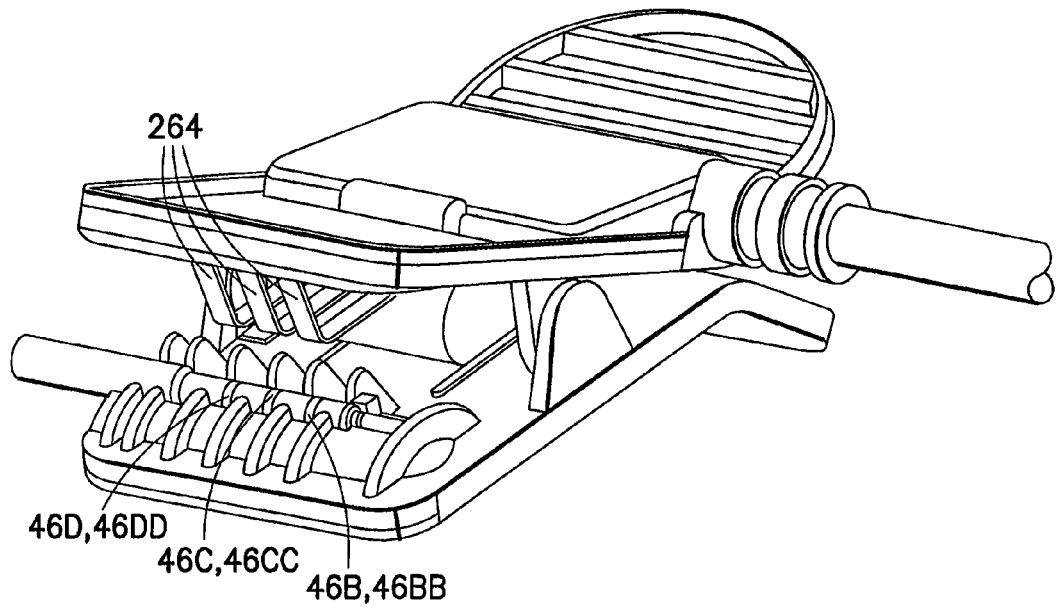

In FIG. 12J, the housing contacts 264 are positioned to engage three contacts, namely, first ring contact 46B or 46BB and second ring contact 46C or 46CC and third ring contact 46D or 46DD of the lead 26 and put them into electrical commonality with PSA 40.

Figure 12K:
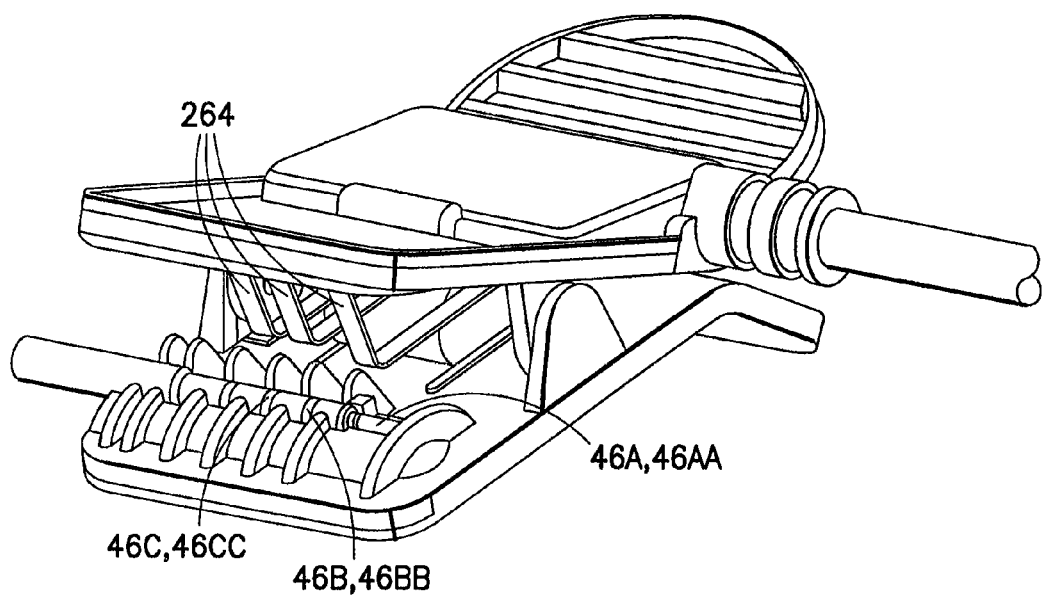

In FIG. 12K, the housing contacts 264 are positioned to engage three contacts, namely, tip contact 46A or 46AA and first ring contact 46B or 46BB and second ring contact 46C or 46CC of the lead 26 and put them into electrical commonality with PSA 40.

Figure 12L:
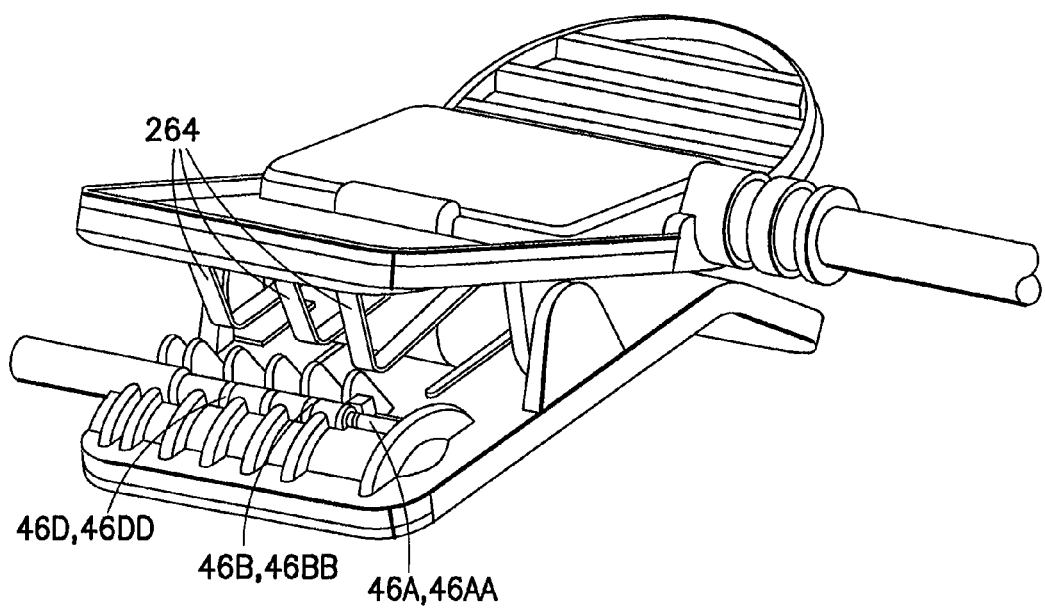

In FIG. 12L, the housing contacts 264 are positioned to engage three contacts, namely, tip contact 46A or 46AA and first ring contact 46B or 46BB and third ring contact 46D or 46DD of the lead 26 and put them into electrical commonality with PSA 40.

Figure 12M:
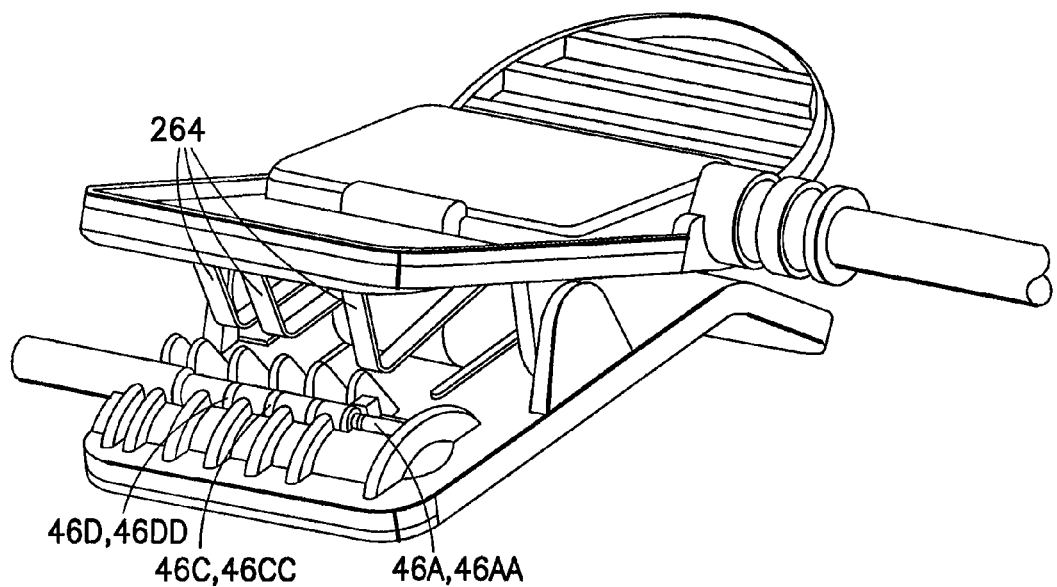

In FIG. 12M, the housing contacts 264 are positioned to engage three contacts, namely, tip contact 46A or 46AA and second ring contact 46C or 46CC and third ring contact 46D or 46DD of the lead 26 and put them into electrical commonality with PSA 40.

Figure 12N:
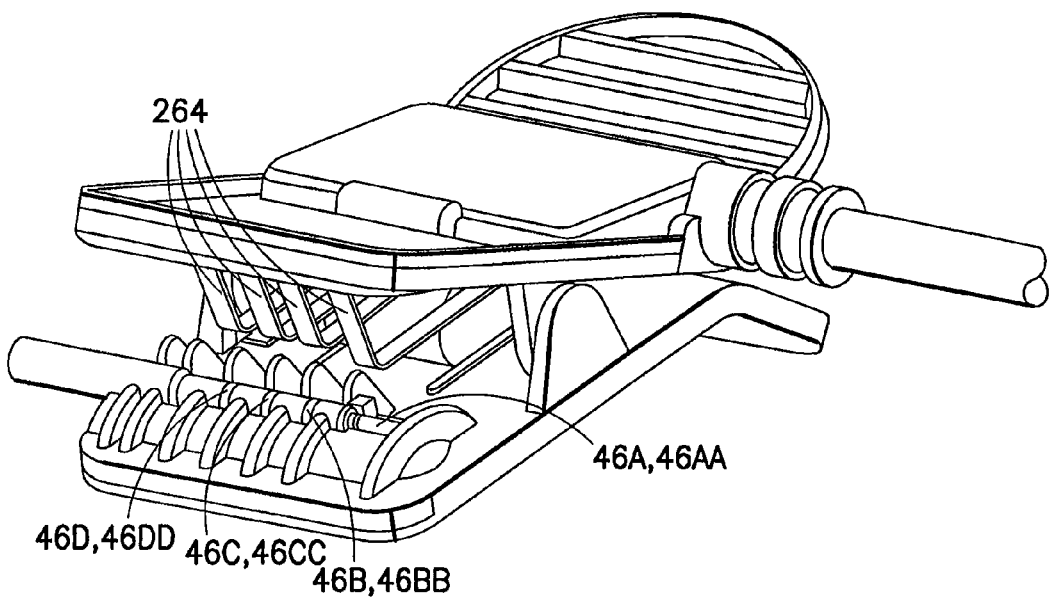

In FIG. 12N, the housing contacts 264 are positioned to engage all four contacts, namely, tip contact 46A or 46AA and first ring contact 46B or 46BB and second ring contact 46C or 46CC and third ring contact 46D or 46DD of the lead 26 and put them all into electrical commonality with PSA 40.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A universal cable connector for detachably connecting an implanted stimulation lead to a patient system analyzer (PSA), the cable connector comprising:
   a nonconductive connector block configured to releasably receive and hold fixed a proximal end of the implanted lead including at least one proximate contact electrically in continuity with a distal electrode at the distal end of the implanted lead;
   a PSA cable configured to selectively electrically interconnect each proximate contact and the PSA; and
   a connector mechanism configured to electrically connect the PSA cable with at least one proximate contact thereby enabling the PSA to determine the efficacy of the chosen body tissue site.

2. The cable connector as set forth in claim 1 wherein the connector block is composed of sterilizable materials.

3. The cable connector as set forth in claim 1 wherein the PSA cable is detachable from the connector block.

4. The cable connector as set forth claim 1 wherein the connector block is disposable.

5. The cable connector as set forth claim 1 wherein the connector block includes:
   a nest region for receiving the proximal end of the implanted lead;
   an upper housing;
   a lower housing with a nest region for receiving the proximal end of the implanted lead;
   a hinge mechanism pivotally mounting the upper housing and the lower housing for relative movement between a raised position whereat the upper housing is distant from the nest region and a lowered position whereat the upper housing is proximate the nest region;
   a resilient member biasing the upper housing toward the lowered position; and
   a housing contact mounted on the upper housing engaged with the exposed at least one proximate contact of the implanted lead when the upper housing is in the lowered position.

* * * * *